United States Patent
Yamaoka et al.

(10) Patent No.: US 8,846,943 B2
(45) Date of Patent: Sep. 30, 2014

(54) PYRROLE DERIVATIVE AND PROCESS FOR PRODUCTION THEREOF

(71) Applicant: Daiichi Sankyo Company, Limited, Tokyo (JP)

(72) Inventors: Makoto Yamaoka, Hiratsuka (JP); Yoshitaka Nakamura, Hiratsuka (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 13/906,526

(22) Filed: May 31, 2013

(65) Prior Publication Data

US 2014/0039198 A1 Feb. 6, 2014

Related U.S. Application Data

(63) Continuation of application No. PCT/JP2011/077616, filed on Nov. 30, 2011.

(30) Foreign Application Priority Data

Dec. 2, 2010 (JP) ................................. 2010-268930

(51) Int. Cl.
*C07D 413/06* (2006.01)
*C07D 263/02* (2006.01)
*C07B 53/00* (2006.01)
*C07D 207/335* (2006.01)

(52) U.S. Cl.
CPC .............. *C07D 413/06* (2013.01); *C07B 53/00* (2013.01); *C07D 207/335* (2013.01)
USPC ........................................................ 548/215

(58) Field of Classification Search
CPC ............................. C07D 413/06; C07D 263/02
USPC ........................................................ 548/215
See application file for complete search history.

(56) References Cited

U.S. PATENT DOCUMENTS

| | | | |
|---|---|---|---|
| 7,910,617 B2 * | 3/2011 | Nishi et al. ..................... | 514/423 |
| 2005/0043386 A1 | 2/2005 | Nishi et al. | |
| 2007/0105933 A1 | 5/2007 | Nishi et al. | |

FOREIGN PATENT DOCUMENTS

| | | |
|---|---|---|
| EP | 1 471 054 | 10/2004 |
| JP | 2005-041867 | 2/2005 |
| JP | 2005-272453 | 10/2005 |
| JP | 2006-188452 | 7/2006 |
| WO | 2003/059880 | 7/2003 |
| WO | 2005/005383 | 1/2005 |

OTHER PUBLICATIONS

Written Opinion of the International Searching Authority issued in corresponding International Application No. PCT/JP2011/077616, mailed on Jan. 24, 2012.
International Search Report issued in corresponding International Application No. PCT/JP2011/077616, mailed on Jan. 24, 2012.
International Preliminary Report on Patentability issued in corresponding International Application No. PCT/JP2011/077616, mailed on Jun. 4, 2013.
Supplementary European Search Report issued in corresponding EP Application No. 11845734.0, dated Mar. 19, 2014.

* cited by examiner

*Primary Examiner* — Kamal Saeed
(74) *Attorney, Agent, or Firm* — Locke Lord, LLP

(57) ABSTRACT

An object of the present invention is to provide a pyrrole derivative useful as an immunosuppressive agent and a method for producing the same. For achieving the object, the present invention provides a method for producing a compound represented by the general formula (I) by heating a compound represented by the general formula (III) and a compound represented by the general formula (IV) in a nonpolar solvent under reduced pressure.

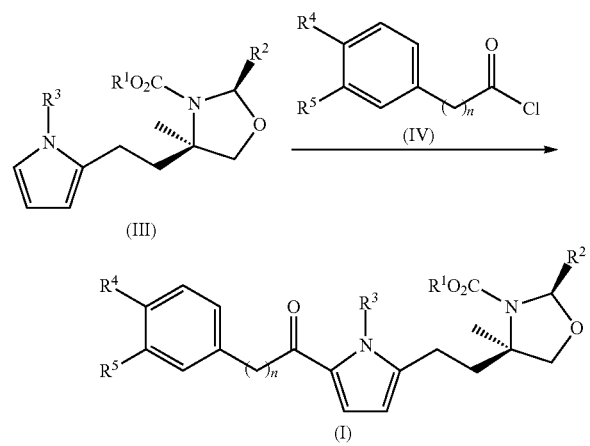

8 Claims, 1 Drawing Sheet

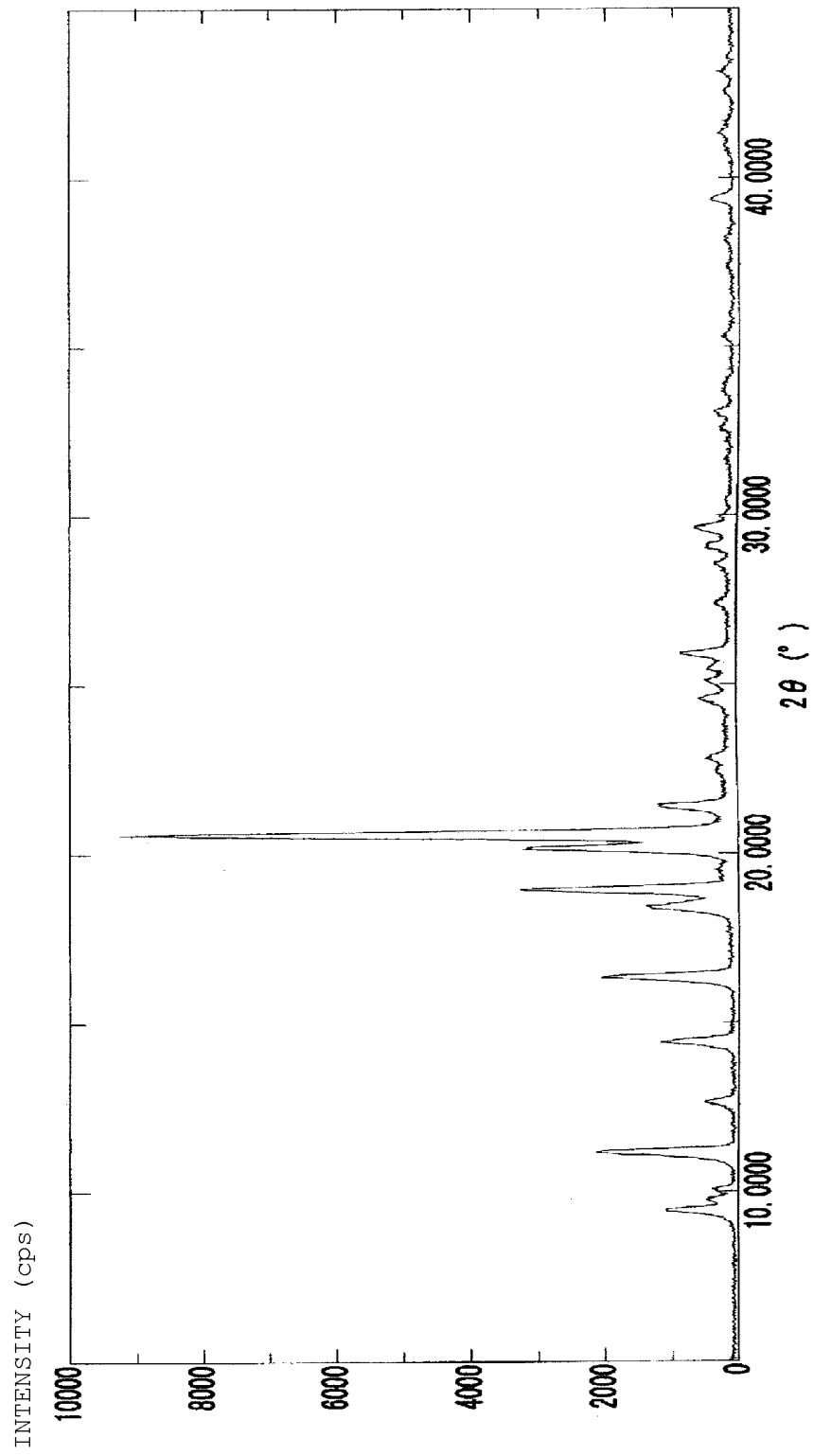

PYRROLE DERIVATIVE AND PROCESS FOR PRODUCTION THEREOF

This application is a continuation of International Application No. PCT/JP2011/077616, filed on Nov. 30, 2011, entitled "PYRROLE DERIVATIVE AND PROCESS FOR PRODUCTION THEREOF", which claims the benefit of Japanese Patent Application Number 2010-268930, filed on Dec. 2, 2010, which is hereby incorporated by reference.

FIELD OF INVENTION

The present invention relates to a pyrrole derivative useful as an immunosuppressive agent and a process for the production thereof.

BACKGROUND

Pyrrole derivatives useful as immunosuppressive agents are known (see, for example, International Publications WO 2003/059880 and WO 2005/079788), and as a method for producing the same, for example, a production method in accordance with the following scheme is disclosed.

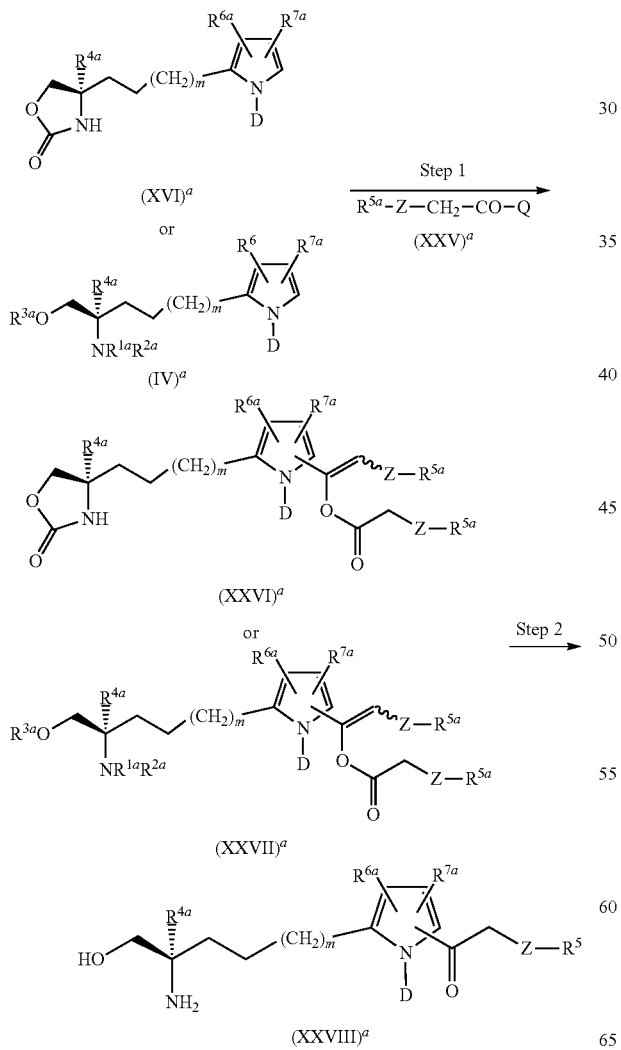

wherein $R^{1a}$ and $R^{2a}$ which are the same or different represent a hydrogen atom, a lower alkyl group or the like; $R^{3a}$ represents a hydrogen atom, a lower alkyl group or the like; $R^{4a}$ represents a lower alkyl group or the like; $R^{5a}$ represents a hydrogen atom, a $C_3$-$C_{10}$ cycloalkyl group, a $C_6$-$C_{10}$ aryl group or the like; $R^{6a}$ and $R^{7a}$ which are the same or different represent a hydrogen atom, a lower alkyl group or the like; m represents an integer of 1 to 6; D represents a lower alkyl group or the like; Z represents a $C_1$-$C_{10}$ alkylene group or the like; and Q represents a halogen atom or the like.

SUMMARY OF THE INVENTION

The present inventors made earnest studies on methods for producing a pyrrole derivative effective as an immunosuppressive agent, and as a result, an excellent industrially applicable production method that overcomes problems of conventional production methods described below has been found out, and thus, the present invention has been accomplished.

Problems of conventional production methods are as follows:

(1) A long reaction time during which heating should be conducted is necessary, and hence problems arise in terms of safety and economy.

(2) The reaction does not go to completion and a raw material remains, and hence, the target compound is only produced in a low yield.

(3) It is necessary to use a large excess amount of reagent for conducting the reaction, and a problem also arises of contamination with a byproduct derived from the reagent.

(4) It is necessary to use silica gel column chromatography for purifying the target compound, but for industrialization, a purification method of lower cost is demanded.

Solution to Problem

The present invention provides:
(1) a compound represented by the general formula (I):

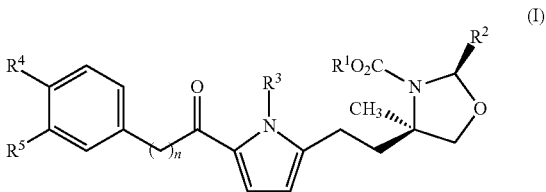

wherein $R^1$ represents a $C_1$-$C_6$ alkyl group or a $C_7$-$C_{12}$ aralkyl group, $R^2$ represents a group selected from the group consisting of a $C_1$-$C_6$ alkyl group, a $C_3$-$C_6$ cycloalkyl group and a $C_7$-$C_{12}$ aralkyl group, $R^3$ represents a $C_1$-$C_6$ alkyl group, $R^4$ and $R^5$ which are the same or different represent a group selected from the group consisting of a hydrogen atom, a halogen atom, a $C_1$-$C_6$ alkyl group, a $C_3$-$C_6$ cycloalkyl group, $C_1$-$C_6$ alkoxy group and a cyano group, and n represents an integer of 1 to 6. Preferably, the present invention provides:

(2) the compound according to (1), wherein $R^1$ is a methyl group, $R^2$ is a t-butyl group, $R^3$ is a methyl group, $R^4$ is a methyl group, $R^5$ is a hydrogen atom, and n is 3.

Furthermore, the present invention provides:
(3) a method for producing a compound represented by the general formula (I) by refluxing a compound represented by the general formula (III) and a compound represented by the general formula (IV), without using a base, in a nonpolar solvent under normal or reduced pressure:

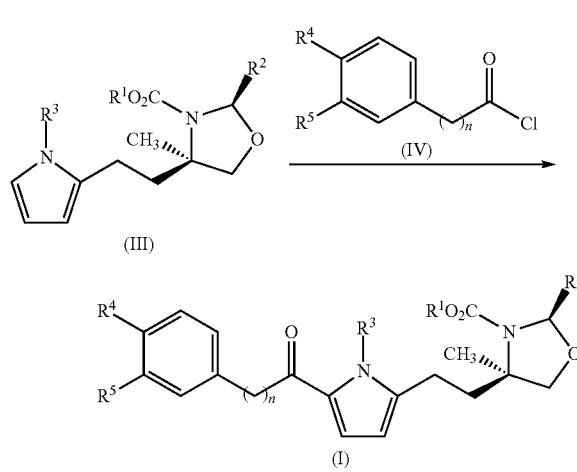

wherein $R^1$ represents a $C_1$-$C_6$ alkyl group or a $C_7$-$C_{12}$ aralkyl group, $R^2$ represents a group selected from the group consisting of a $C_1$-$C_6$ alkyl group, a $C_3$-$C_6$ cycloalkyl group and a $C_7$-$C_{12}$ aralkyl group, $R^3$ represents a $C_1$-$C_6$ alkyl group, $R^4$ and $R^5$ which are the same or different represent a group selected from the group consisting of a hydrogen atom, a halogen atom, a $C_1$-$C_6$ alkyl group, a $C_3$-$C_6$ cycloalkyl group, a $C_1$-$C_6$ alkoxy group and a cyano group, and n represents an integer of 1 to 6.

Preferably, the present invention provides:

(4) the method for producing a compound represented by the general formula (I) according to (3), wherein $R^1$ is a methyl group, $R^2$ is a t-butyl group, $R^3$ is a methyl group, $R^4$ is a methyl group, $R^5$ is a hydrogen atom, and n is 3;

(5) a method for producing a compound represented by the general formula (II) in which a compound represented by the general formula (I) is produced by refluxing a compound represented by the general formula (III) and a compound represented by the general formula (IV), without using a base, in a nonpolar solvent under normal or reduced pressure, and the compound represented by the general formula (I) is treated with an acid and an alkali in this order:

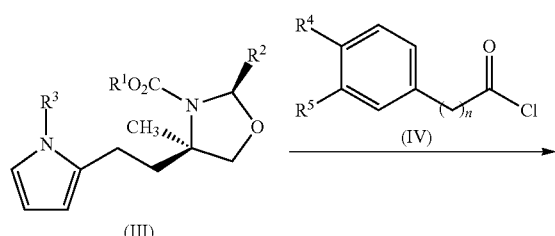

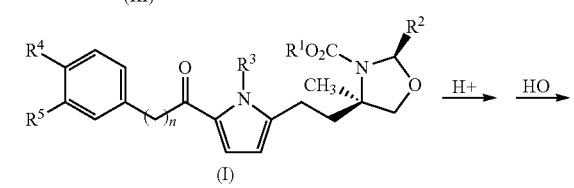

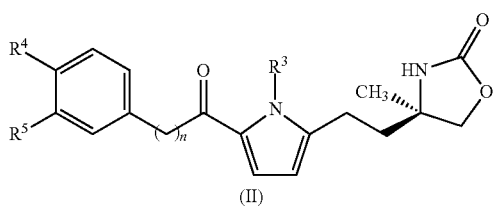

wherein $R^1$ represents a $C_1$-$C_6$ alkyl group or a $C_7$-$C_{12}$ aralkyl group, $R^2$ represents a group selected from the group consisting of a $C_1$-$C_6$ alkyl group, a $C_3$-$C_6$ cycloalkyl group and a $C_7$-$C_{12}$ aralkyl group, $R^3$ represents a $C_1$-$C_6$ alkyl group, $R^4$ and $R^5$ which are the same or different represent a group selected from the group consisting of a hydrogen atom, a halogen atom, a $C_1$-$C_6$ alkyl group, a $C_3$-$C_6$ cycloalkyl group, a $C_1$-$C_6$ alkoxy group and a cyano group, and n represents an integer of 1 to 6;

(6) the method for producing a compound represented by the general formula (II) according to (5), wherein $R^1$ is a methyl group, $R^2$ is a t-butyl group, $R^3$ is a methyl group, $R^4$ is a methyl group, $R^5$ is a hydrogen atom, and n is 3;

(7) a method for producing a compound represented by the general formula (V) in which a compound represented by the general formula (I) is produced by refluxing a compound represented by the general formula (III) and a compound represented by the general formula (IV), without using a base, in a nonpolar solvent under normal or reduced pressure, a compound represented by the general formula (II) is produced by treating the compound represented by the general formula (I) with an acid and an alkali in this order, and the compound represented by the general formula (II) is treated with an alkali:

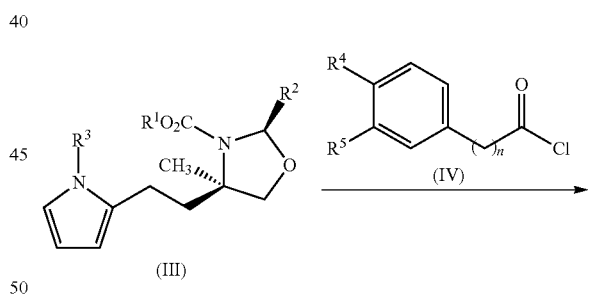

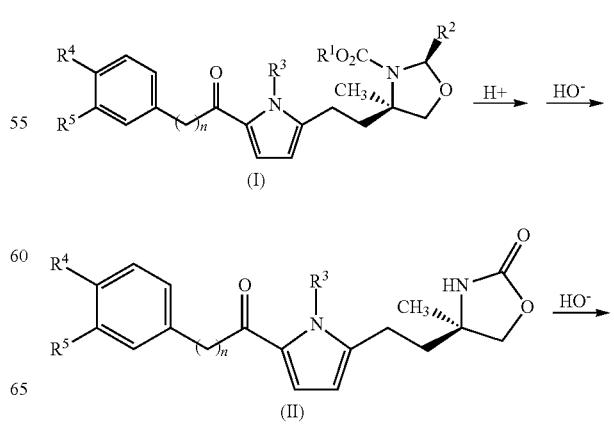

-continued

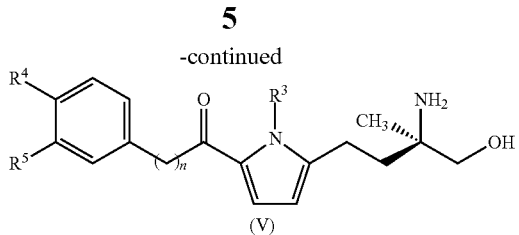

(V)

wherein $R^1$ represents a $C_1$-$C_6$ alkyl group or a $C_7$-$C_{12}$ aralkyl group, $R^2$ represents a group selected from the group consisting of a $C_1$-$C_6$ alkyl group, a $C_3$-$C_6$ cycloalkyl group and a $C_7$-$C_{12}$ aralkyl group, $R^3$ represents a $C_1$-$C_6$ alkyl group, $R^4$ and $R^5$ which are the same or different represent a group selected from the group consisting of a hydrogen atom, a halogen atom, a $C_1$-$C_6$ alkyl group, a $C_3$-$C_6$ cycloalkyl group, a $C_1$-$C_6$ alkoxy group and a cyano group, and n represents an integer of 1 to 6; and (8) the method for producing a compound represented by the general formula (V) according to (7), wherein $R^1$ is a methyl group, $R^2$ is a t-butyl group, $R^3$ is a methyl group, $R^4$ is a methyl group, $R^5$ is a hydrogen atom, and n is 3.

The "$C_1$-$C_6$ alkyl group" of the present invention refers to a straight or branched alkyl group having 1 to 6 carbon atoms, and is, for example, a methyl group, an ethyl group, a propyl group, an isopropyl group, a butyl group, an isobutyl group, a t-butyl group, a pentyl group or a hexyl group.

The "$C_7$-$C_{12}$ aralkyl group" of the present invention refers to an aryl-substituted methylene group which may be substituted by a $C_1$-$C_6$ alkyl group, and is, for example, a benzyl group, a 4-methylphenylmethyl group, an indenylmethyl group or a naphthylmethyl group.

The "$C_3$-$C_6$ cycloalkyl group" of the present invention refers to a cyclic alkyl group having 3 to 6 carbon atoms, and is, for example, a cyclopropyl group, a cyclobutyl group, a cyclopentyl group or a cyclohexyl group.

The "$C_1$-$C_6$ alkoxy group" of the present invention refers to a $C_1$-$C_6$ alkyl group bonded to an oxygen atom, and is, for example, a methoxy group, an ethoxy group, a propoxy group, an isopropoxy group, a butoxy group, an isobutoxy group, a t-butoxy group, a pentyloxy group or a hexyloxy group.

"$R^1$" of the present invention is preferably a methyl group, an ethyl group, a t-butyl group or a benzyl group, and more preferably a methyl group.

"$R^2$" of the present invention is preferably an isopropyl group, a t-butyl group or a benzyl group, and more preferably a t-butyl group.

"$R^3$" of the present invention is preferably a methyl group or an ethyl group, and more preferably a methyl group.

"$R^4$" of the present invention is preferably a fluorine atom, a chlorine atom, a methyl group, a methoxy group or a cyano group, and more preferably a methyl group.

"$R^5$" of the present invention is preferably a hydrogen atom, a chlorine atom, a methyl group or a methoxy group, and more preferably a hydrogen atom.

"n" of the present invention is preferably 3, 4 or 5, and more preferably 3.

Advantageous Effects of Invention

The compounds respectively represented by the general formula (I) and the general formula (II) of the present invention are useful as intermediates for an immunosuppressive agent, that is, the compound represented by the general formula (V) (International Publication No. WO2003/059880). The present invention is also useful because the compound represented by the general formula (V) can be produced by an industrially applicable production method in which conventional problems that occur when using these intermediates are overcome.

BRIEF DESCRIPTION OF DRAWINGS

FIG. 1 is a diagram of an X-ray powder diffraction pattern of crystal of Compound (1), in which the abscissa indicates the incident angle and the ordinate indicates diffraction intensity. One peak corresponds to one crystal face.

DETAILED DESCRIPTION

As described below, a compound represented by the general formula (I) can be produced by refluxing a compound represented by the general formula (III) and a compound represented by the general formula (IV), without using a base, in a nonpolar solvent under normal or reduced pressure.

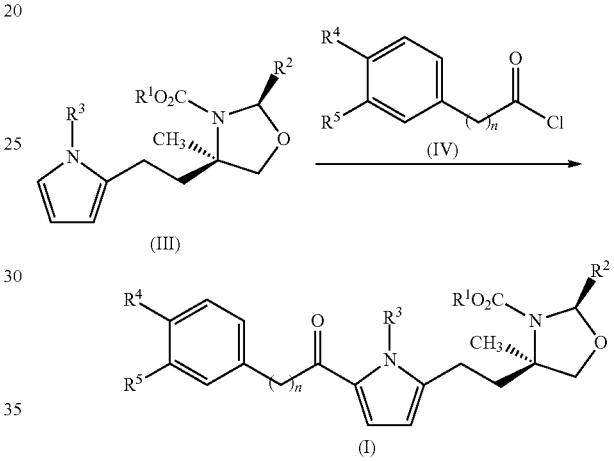

wherein $R^1$, $R^2$, $R^3$, $R^4$, $R^5$ and n have the same meanings as defined above.

The "normal or reduced pressure" employed in this reaction may be any pressure at which hydrogen chloride gas generated in accordance with the progress of the reaction may be removed from the reaction system and the solvent is not distilled off excessively, and is preferably 20 to 120 kPa and more preferably 40 to 100 kPa.

The term "without using a base" used with respect to this reaction means that a base used in the field of organic synthesis, such as a base used in general acylation, is not used. According to the present invention, it has been found through earnest examination that the target reaction is prevented and a side reaction is caused if a base regarded to be generally necessary in acylation is used and that the target reaction progresses in a higher yield when a base is not used.

The "nonpolar solvent" used in this reaction is a solvent generally having a low dielectric constant or a low dipole moment, and one having low solubility for hydrogen chloride gas is preferred. Examples of the nonpolar solvent include aliphatic hydrocarbons such as hexane, methylcyclohexane, ethylcyclohexane, heptane, ligroin and petroleum ether; aromatic hydrocarbons such as toluene, benzene and xylene; and halogenated hydrocarbons such as dichloromethane, chloroform, carbon tetrachloride, dichloroethane, chlorobenzene and dichlorobenzene, of which the aliphatic hydrocarbons and the aromatic hydrocarbons are preferably used, and methylcyclohexane, ethylcyclohexane, toluene and xylene are more preferably used.

The term "refluxing" used with respect to this reaction refers to a state where the solvent is always repeatedly boiled and condensed for conducting the reaction. In this reaction, hydrogen chloride gas may be preferably removed from the reaction solution by refluxing the solvent. Accordingly, the heating temperature is varied depending upon the solvent to be used, and is preferably 50 to 180° C. and more preferably 70 to 150° C.

The reaction time of this reaction is generally 5 minutes to 48 hours and preferably 1 to 24 hours.

Furthermore, according to the present invention, a compound represented by the general formula (V) may be produced by subjecting a compound represented by the general formula (II), which has been obtained by conducting (1) an acid treatment and (2) an alkali treatment in this order on the compound represented by the general formula (I), to (3) another alkali treatment.

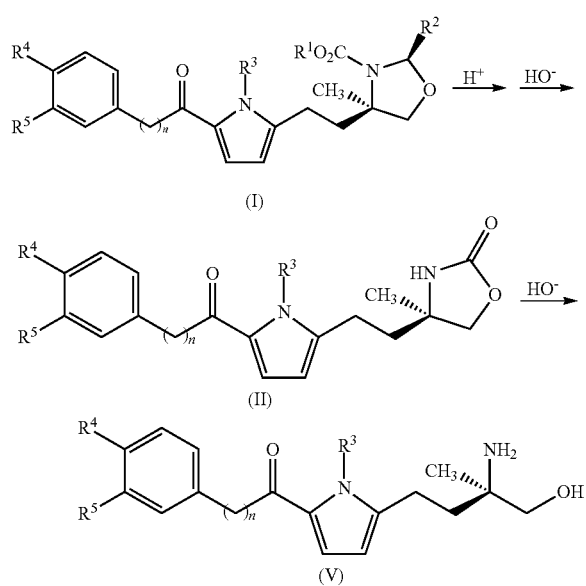

wherein $R^1$, $R^2$, $R^3$, $R^4$, $R^5$ and n have the same meanings as defined above.

(1) Acid Treatment Step

The acid to be used for this reaction is not especially limited as long as it is an acid generally used for deprotection of an acetal group, and examples of the acid include inorganic acids such as (concentrated) hydrochloric acid, hydrobromic acid, sulfuric acid, perchloric acid and phosphoric acid; Bronsted acids of organic acids or the like such as acetic acid, formic acid, oxalic acid, methanesulfonic acid, p-toluenesulfonic acid, camphorsulfonic acid, trifluoroacetic acid and trifluoromethanesulfonic acid; Lewis acids such as zinc chloride, tin tetrachloride, boron trichloride, boron trifluoride and boron tribromide; and acidic ion-exchange resins, and inorganic acids (of which concentrated hydrochloric acid is particularly preferred) are preferably used.

Any inert solvent used in the reaction is not especially limited as long as it is inert to this reaction. Examples of such a solvent include ethers such as diethyl ether, diisopropyl ether, tetrahydrofuran, dioxane, dimethoxyethane, and diethylene glycol dimethyl ether; alcohols such as methanol, ethanol, n-propanol, isopropanol, n-butanol, isobutanol, t-butanol and diethylene glycol; and water. Alcohols (of which methanol is the most preferred), water and mixed solvents of water and the above-described organic solvents are preferably used, and a mixed solvent of water and methanol is particularly preferably used.

The reaction temperature is generally 0 to 100° C. (preferably 20 to 80° C.).

The reaction time is generally 30 minutes to 48 hours (preferably 1 to 10 hours).

(2) Alkali Treatment Step

The base to be used in this reaction is not especially limited as long as it is generally used as a base and does not inhibit the reaction. Examples of the base include alkali metal carbonates such as lithium carbonate, sodium carbonate and potassium carbonate; alkali metal hydroxides such as lithium hydroxide, sodium hydroxide and potassium hydroxide; metal alkoxides such as lithium methoxide, sodium methoxide, sodium ethoxide and potassium-t-butoxide; and ammonias such as aqueous ammonia and concentrated ammonia-methanol. Alkali metal hydroxides are preferably used, and sodium hydroxide (such as a 25% sodium hydroxide aqueous solution) is more preferably used.

Any inert solvent used in the reaction is not especially limited as long as it is inert to this reaction. Examples of the solvent include ethers such as diethyl ether, diisopropyl ether, tetrahydrofuran, dioxane, dimethoxyethane, and diethylene glycol dimethyl ether; alcohols such as methanol, ethanol, n-propanol, isopropanol, n-butanol, isobutanol, t-butanol and diethylene glycol; and water. Alcohols (of which methanol is the most preferred), water and mixed solvents of water and the above-described organic solvents are preferably used, and a mixed solvent of water and methanol is particularly preferably used.

The reaction temperature varies depending upon the kinds of raw material compound, reagent, solvent, and the like to be used, and is generally 0 to 100° C. (preferably 20 to 80° C.)

The reaction time is generally 5 minutes to 10 hours (preferably 30 minutes to 5 hours).

(3) Alkali Treatment Step

The base to be used in this reaction is not especially limited as long as it is generally used as a base and does not inhibit the reaction. Examples of the base include alkali metal carbonates such as lithium carbonate, sodium carbonate and potassium carbonate; alkali metal hydroxides such as lithium hydroxide, sodium hydroxide and potassium hydroxide; metal alkoxides such as lithium methoxide, sodium methoxide, sodium ethoxide and potassium-t-butoxide; and ammonias such as aqueous ammonia and concentrated ammonia-methanol. Alkali metal hydroxides are preferably used, and sodium hydroxide (such as a 25% sodium hydroxide aqueous solution) is more preferably used.

Any inert solvent used in the reaction is not especially limited as long as it is inert to this reaction. Examples of the solvent include ethers such as diethyl ether, diisopropyl ether, tetrahydrofuran, dioxane, dimethoxyethane and diethylene glycol dimethyl ether; alcohols such as methanol, ethanol, n-propanol, isopropanol, n-butanol, isobutanol, t-butanol and diethylene glycol; and water. Alcohols (of which propanol and n-butanol are particularly preferred), water and mixed solvents of water and the above-described organic solvents are preferably used, and a mixed solvent of n-propanol or n-butanol and water is preferably used.

The reaction temperature is generally 0 to 150° C. (preferably 60 to 120° C.)

The reaction time is generally 30 minutes to 20 hours (preferably 1 to 10 hours).

EXAMPLES

The present invention will now be specifically described with reference to examples, but the present invention is not limited to these examples. NMR spectra were measured by using tetramethylsilane as internal standard, and all δ values were expressed in ppm.

Incidentally, compounds and solvents described in the following examples have the following meanings:

Compound (1):
1-{5-[(3R)-3-amino-4-hydroxy-3-methylbutyl]-1-methyl-1H-pyrrol-2-yl}-4-(4-methylphenyl)butan-1-one Compound (2):
methyl (2R,4R)-2-t-butyl-4-methyl-4-[2-(1-methyl-1H-pyrrol-2-yl)ethyl]-1,3-oxazolidine-3-carboxylate (or (2R,4R)-2-t-butyl-4-methyl-4-[2-(1-methyl-1H-pyrrol-2-yl)ethyl]-1,3-oxazolidine-3-carboxylic acid methyl ester)

Compound (3):
methyl (2R,4R)-2-t-butyl-4-methyl-4-(2-{1-methyl-5-[4-(4-methylphenyl)butanoyl]-1H-pyrrol-2-yl}ethyl)-1,3-oxazolidine-3-carboxylate (or (2R,4R)-2-t-butyl-4-methyl-4-(2-{1-methyl-5-[4-(4-methylphenyl)butanoyl]-1H-pyrrol-2-yl}ethyl)-1,3-oxazolidine-3-carboxylic acid methyl ester)

Compound (4):
methyl N-((1R-1-(hydroxymethyl)-1-methyl-3-{1-methyl-5-[4-(4-methylphenyl)butanoyl]-1H-pyrrol-2-yl}propyl)carbamate Compound (5):
(4R)-4-methyl-4-(2-{1-methyl-5-[4-(4-methylphenyl)butanoyl]-1H-pyrrol-2-yl}ethyl)-1,3-oxazolidin-2-one MCH: methylcyclohexane
ECH: ethylcyclohexane
DMF: N,N-dimethylformamide Example 1

Method for Producing Compound (1)

(1-1) Preparation of 4-(4-methylphenyl)butyryl chloride

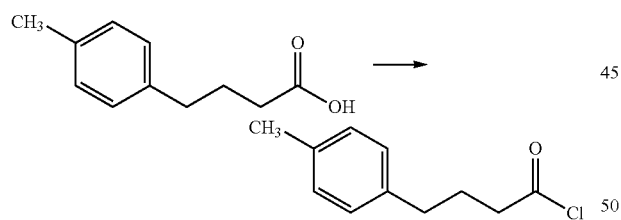

4-(4-Methylphenyl)butyryl chloride (20.8 g) was dissolved in MCH (95 mL), and to the resulting solution, DMF (90 μL) and oxalyl chloride (15.9 g) were added at room temperature under a nitrogen atmosphere. After stirring the resulting solution at that temperature for 2 hours, the MCH was distilled off at a degree of reduced pressure of 2.7 to 7.5 kPa and an external temperature of 60° C. (an internal temperature of approximately 50 to 60° C.). MCH (36 mL) was added thereto again and was distilled off at a degree of reduced pressure of 2.7 to 7.5 kPa and an external temperature of 60° C. (an internal temperature of approximately 50 to 60° C.) The thus prepared 4-(4-methylphenyl)butyryl chloride solution was allowed to stand overnight under a nitrogen atmosphere, and then was used for acylation (1-2) without purification.

(1-2) Step of Producing Compound (3) by Using Compound (2) as Raw Material

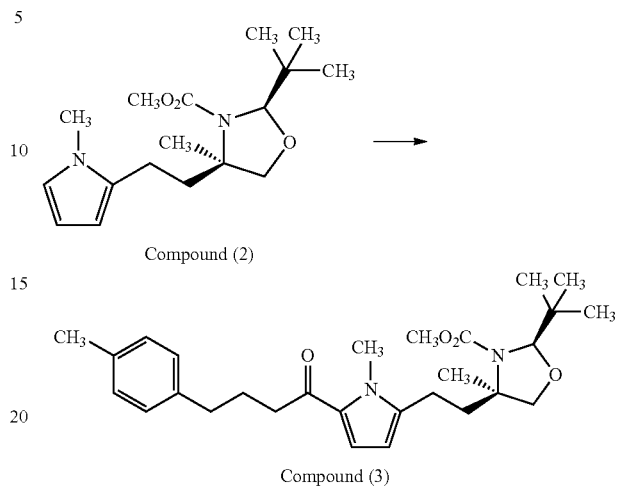

MCH (45 mL) was added to Compound (2) (18.0 g), and the resultant was heated and refluxed, and after the prepared 4-(4-methylphenyl)butyryl chloride solution was added dropwise thereto so as to maintain the reflux state, the reaction solution was stirred for 4 hours under reflux. The reaction solution was cooled to 50° C., and then, a 25% sodium hydroxide aqueous solution (23.3 g), tap water (54 mL) and MCH (54 mL) were added thereto, followed by stirring for 1 hour at that temperature. The resulting solution was separated to obtain an organic layer. Subsequently, 28% sodium methoxide (1.7 g) was added thereto, and the resultant was stirred for 30 minutes, tap water (54 mL) was added thereto, and the resulting solution was separated so as to obtain an organic layer. After distilling off the organic layer to approximately 54 mL (an internal temperature of approximately 50 to 60° C.), n-propanol (90 mL) was added thereto, followed by distilling off again to 54 mL. To the thus obtained solution, n-propanol (126 mL) and tap water (153 mL) were added, and seed crystal (20 mg) of Compound (3) was inoculated in the resulting solution at an internal temperature of approximately 40° C., followed by stirring for 1 hour. Thereafter, the resulting solution was cooled to an internal temperature of approximately 0° C. and stirred for 1 hour, and the obtained crystal was filtered, washed and dried, so as to obtain a crystal of Compound (3) (24.4 g, yield: 89.4%).

Analysis Data

Methyl (2R,4R)-2-t-butyl-4-methyl-4-(2-{1-methyl-5-[4-(4-methylphenyl)butanoyl]-1H-pyrrol-2-yl}ethyl)-1,3-oxazolidine-3-carboxylate (Compound (3))

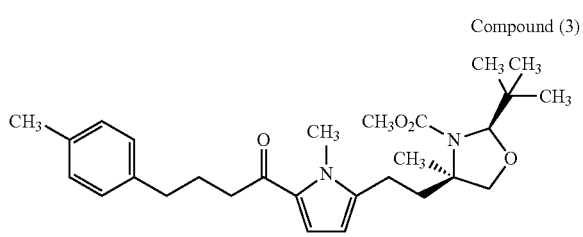

Compound (3)

$^1$H NMR (CDCl$_3$, 400 MHz): 0.95 (s, 9H), 1.41 (s, 3H), 1.95-2.10 (m, 3H), 2.30 (s, 3H), 2.30-2.40 (m, 1H), 2.50-2.70 (m, 4H), 2.73 (t, 2H, J=7.4 Hz), 3.68 (s, 3H), 3.68 (d, 1H, J=8.8 Hz), 3.85 (s, 3H), 3.97 (d, 1H, J=8.8 Hz), 5.13 (s, 1H), 5.92 (d, 1H, J=4.4 Hz), 6.85 (d, 1H, J=4.4 Hz), 7.00-7.10 (m, 4H)

$^{13}$C NMR (CDCl$_3$, 100 MHz): 20.9, 22.2, 22.3, 26.5, 27.0, 32.9, 34.9, 36.4, 38.4, 38.4, 52.0, 63.7, 77.5, 97.2, 106.6, 118.9, 128.3, 128.9, 130.7, 135.2, 138.8, 141.9, 156.4, 190.7

MS (FAB): m/z=469 [M+H]$^+$ (1-3) Step of Producing Compound (1) by Using Compound (3) as Raw Material

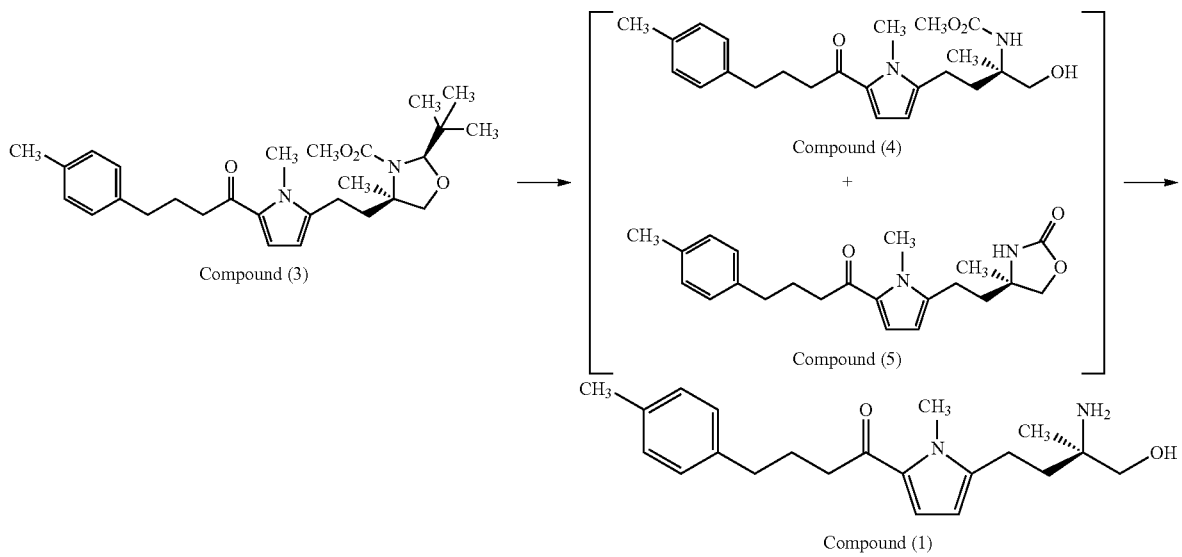

(1-3-1) Step of Deacetalization of N,O-acetal

Methanol (360 mL) was added to Compound (3) (30 g), the resultant was heated to 45° C. for dissolving, and concentrated hydrochloric acid (2.6 mL) was added thereto. After stirring at that temperature for 3 hours, a 25% sodium hydroxide aqueous solution (46.7 mL) was added thereto for stopping the reaction. After cooling to room temperature, the reaction solution was concentrated under reduced pressure until a five-fold amount (150 mL) was attained. Thereafter, n-propanol (300 mL) was added thereto, and the concentration was conducted under reduced pressure again until a five-fold amount (150 mL) was attained, so as to obtain a solution of a mixture of Compound (4) and Compound (5) in n-propanol. The solution of the mixture of Compound (4) and Compound (5) in n-propanol thus obtained was used in the following step without purification.

(1-3-2) Step of Decarbonylation

To the solution of the mixture of Compound (4) and Compound (5) in n-propanol obtained in the previous step, n-propanol was added until a seven-fold amount (210 mL) was attained. To the resultant, tap water (30 mL) and a 25% sodium hydroxide aqueous solution (51.2 mL) were added, followed by heating to attain reflux. The reaction solution was stirred for 7 hours under reflux and then cooled to room temperature, and toluene (300 mL) and tap water (300 mL) were added thereto, followed by separation. The thus obtained organic layer was concentrated under reduced pressure until a five-fold amount (150 mL) was attained. To the resultant, toluene (300 mL) was added, followed by concentration again carried out under reduced pressure until a five-fold amount (150 mL) was attained. To the thus concentrated solution, toluene was added until a ten-fold amount (300 mL) was attained, MCH (300 mL) was further added thereto, and the resultant was stirred at room temperature for 30 minutes and then was cooled to 5° C. or lower. After stirring for 30 minutes at that temperature, precipitated crystal was filtered and washed with a mixed solvent of cooled toluene and MCH (mixing ratio: 1/2). The crystal was vacuum dried at 40° C. for 10 or more hours, so as to obtain a crude crystal of Compound (1) (20.4 g, yield: 93.2%).

(1-3-3) Step of Purification

After adding methanol (285 mL) to the crude crystal (19.0 g) obtained in the previous step for dissolving, the resulting solution was concentrated under reduced pressure until a five-fold amount (150 mL) was attained. To the thus concentrated solution, methanol was added until a ten-fold amount (190 mL) was attained, and tap water (190 mL) was further added thereto with the temperature maintained at 25 to 40° C. The external temperature was set to 20° C., and the reaction solution was slowly cooled until crystal was precipitated, and was stirred for 30 minutes at the temperature of crystallization. To the reaction solution, tap water (190 mL) was added, and the resulting solution was further cooled to 5° C. or lower, followed by stirring for 30 minutes. Thereafter, the thus precipitated crystal was filtered and washed with 33% cooled aqueous methanol. The crystal was vacuum dried at 40° C. for 10 or more hours, so as to obtain a crystal of Compound (1) (18.4 g, yield: 97.0%).

Example 2

Method for Producing Compound (1)

(2-1) Preparation of 4-(4-methylphenyl)butyryl chloride 4-(4-Methylphenyl)butyryl chloride (8.66 g) was dissolved in ECH (70 mL), and to the resulting solution, DMF (10 μL) and oxalyl chloride (4.5 mL) were added at room temperature under a nitrogen atmosphere. After stirring the thus obtained solution at that temperature for 3 hours, the ECH (10 mL) was distilled off with a degree of reduced pressure set to 6.5 kPa and an external temperature set to 75° C. (an internal temperature of approximately 54° C.). The thus prepared solution (the solution of 4-(4-methylphenyl) butyryl chloride in ECH) was allowed to stand overnight under a nitrogen atmosphere, and then was used for acylation (2-2) without purification.

(2-2) Step of Producing Compound (5) by Using Compound (2) as Raw Material

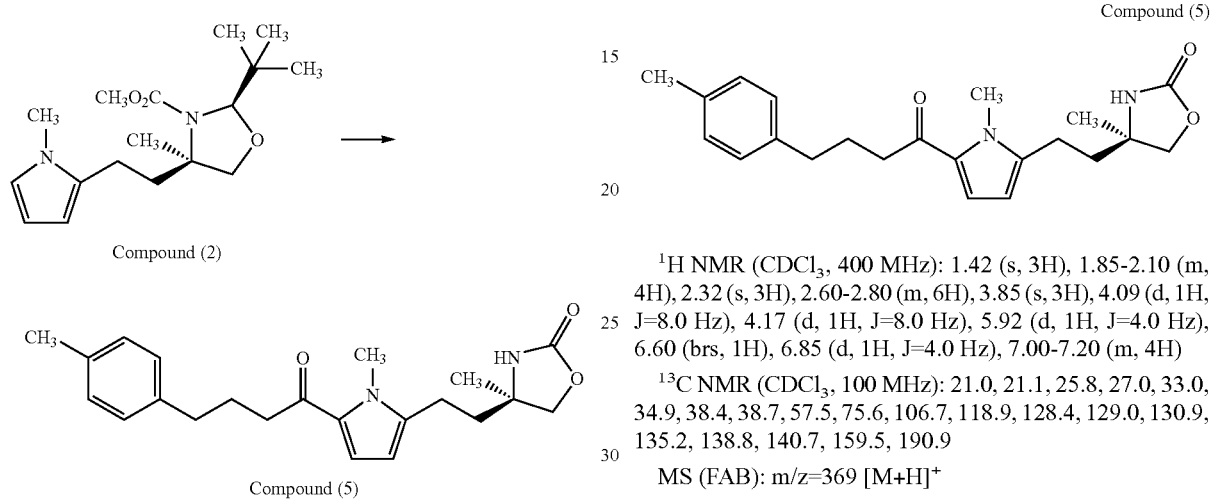

After adding Compound (2) (10 g) to the solution of 4-(4-methylphenyl)butyryl chloride in ECH at room temperature under a nitrogen atmosphere, the ECH (10 mL) was distilled off with the degree of reduced pressure set to 45 kPa and the external temperature set to 135° C. (an internal temperature of approximately 106° C.). With the external temperature maintained, the degree of reduced pressure was changed to 55 kPa, and the reaction solution was stirred for 8 hours under reflux. The reaction solution was cooled to 50° C., a 25% sodium hydroxide aqueous solution (7.8 mL) and tap water (30 mL) were added thereto, and the resulting solution was stirred at that temperature for 1 hour, and then was allowed to stand overnight. ECH (50 mL) was added to the thus obtained solution, and the resultant was heated to 50° C. After separating the solution at that temperature to remove the aqueous layer, tap water (30 mL) was added to the thus obtained ECH layer and the resulting solution was separated again, so as to obtain an organic layer. The organic layer was concentrated under reduced pressure until a five-fold amount (50 mL) was attained, and to the resultant, methanol (100 mL) and hydrochloric acid (2.7 mL) were added, followed by heating to 50° C. After stirring at that temperature for 2.5 hours, a 25% sodium hydroxide aqueous solution (4.6 mL) and tap water (20 mL) were added thereto, followed by heating to 50° C. After stirring at that temperature for 1.0 hour, the resulting solution was separated to remove the ECH layer. The thus obtained aqueous methanol layer was cooled to 30° C., and seed crystal of Compound (5) was inoculated therein. After confirming crystallization, tap water (30 mL) was added thereto, the resultant was stirred for 1.0 hour at that temperature, followed by cooling to 5° C. or lower. After stirring at that temperature for 30 minutes, precipitated crystal was filtered and washed with cooled 70% aqueous methanol. The crystal was vacuum dried at 50° C. for 10 or more hours, so as to obtain a crystal of Compound (5) (10.6 g, yield: 88.6%).

Analysis Data (4R)-4-Methyl-4-(2-{1-methyl-5-[4-(4-methylphenyl)butanoyl]-1H-pyrrol-2-yl}ethyl)-1,3-oxazolidin-2-one (Compound (5))

Compound (5)

$^1$H NMR (CDCl$_3$, 400 MHz): 1.42 (s, 3H), 1.85-2.10 (m, 4H), 2.32 (s, 3H), 2.60-2.80 (m, 6H), 3.85 (s, 3H), 4.09 (d, 1H, J=8.0 Hz), 4.17 (d, 1H, J=8.0 Hz), 5.92 (d, 1H, J=4.0 Hz), 6.60 (brs, 1H), 6.85 (d, 1H, J=4.0 Hz), 7.00-7.20 (m, 4H)

$^{13}$C NMR (CDCl$_3$, 100 MHz): 21.0, 21.1, 25.8, 27.0, 33.0, 34.9, 38.4, 38.7, 57.5, 75.6, 106.7, 118.9, 128.4, 129.0, 130.9, 135.2, 138.8, 140.7, 159.5, 190.9

MS (FAB): m/z=369 [M+H]$^+$

Incidentally, when Compound (3) was used as a raw material, Compound (5) was produced as follows.

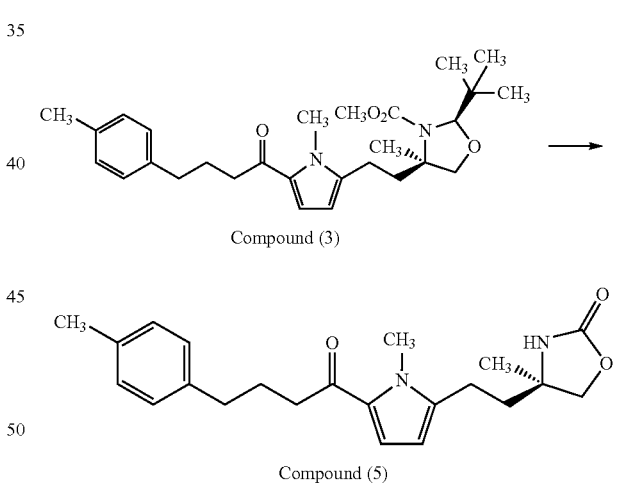

Methanol (132 mL) and concentrated hydrochloric acid (2.3 mL) were added to Compound (3) (22.0 g), and the resulting solution was heated to 45 to 50° C., followed by stirring for 2.5 hours. After adding a 25% sodium hydroxide aqueous solution (4.5 g) thereto, the resulting solution was stirred for 2 hours at that temperature and then cooled to an internal temperature of 20 to 25° C. After inoculating seed crystal of Compound (5) therein, tap water (103 mL) was added thereto, followed by stirring at that temperature for 1 hour. The thus obtained crystal was filtered, washed and dried, so as to obtain a crystal of Compound (5) (16.3 g, yield: 94.5%).

(2-3) Step of Producing Compound (1) by Using Compound (5) as Raw Material

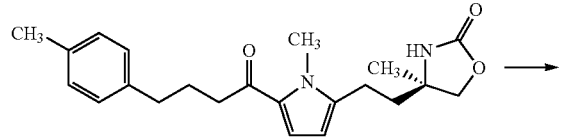

Compound (5)

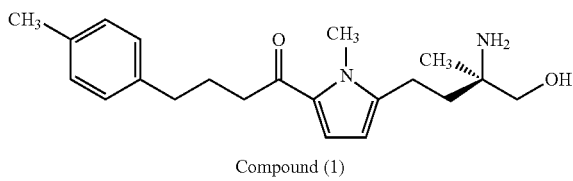

Compound (1)

To the crystal (15.0 g) of Compound (5), n-butanol (90 mL) and a 25% sodium hydroxide aqueous solution (32.5 g) were added, and the resulting solution was heated and refluxed. After stirring for 5 hours under reflux, the reaction solution was cooled to approximately 60° C., and tap water (45 mL) was added thereto, followed by separation. The thus obtained organic layer was concentrated under reduced pressure to 45 mL, heptane (60 mL) was added thereto, and the resultant was concentrated under reduced pressure again to 45 mL. The thus obtained concentrated solution was adjusted to an internal temperature of 40 to 45° C., and heptane (195 mL) was added thereto for precipitating crystal. After stirring for 30 minutes, the resulting solution was cooled to an internal temperature of 5° C. or lower. After stirring at that temperature for 1 hour, the crystal was filtered, washed and dried, so as to obtain a crystal of Compound (1) (12.0 g, yield: 86.2%).

Analysis Data

1-{5-[(3R)-3-Amino-4-hydroxy-3-methylbutyl]-1-methyl-1H-pyrrol-2-yl}-4-(4-methylphenyl)butan-1-one (Compound (1))

Compound (1)

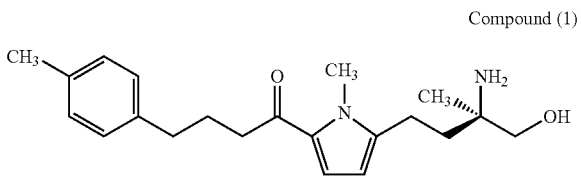 [SMILES: Cc1ccc(CCCC(=O)c2ccc(CC[C@@](C)(N)CO)n2C)cc1]

The crystal of Compound (1) showed an X-ray powder diffraction pattern as illustrated in FIG. 1. Since a sharp diffraction peak was observed, it was confirmed that Compound (1) was crystalline.

The invention claimed is:

1. A compound of formula (I):

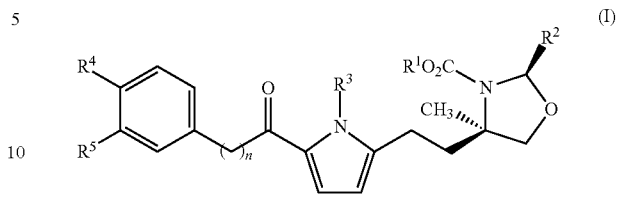

wherein
R$^1$ represents a C$_1$-C$_6$ alkyl group or a C$_7$-C$_{12}$ aralkyl group,
R$^2$ represents a group selected from the group consisting of a C$_1$-C$_6$ alkyl group, a C$_3$-C$_6$ cycloalkyl group and a C$_7$-C$_{12}$ aralkyl group,
R$^3$ represents a C$_1$-C$_6$ alkyl group,
R$^4$ and R$^5$ which are the same or different represent a group selected from the group consisting of a hydrogen atom, a halogen atom, a C$_1$-C$_6$ alkyl group, a C$_3$-C$_6$ cycloalkyl group, C$_1$-C$_6$ alkoxy group and a cyano group, and
n represents an integer of 1 to 6.

2. The compound according to claim 1, wherein R$^1$ is a methyl group, R$^2$ is a t-butyl group, R$^3$ is a methyl group, R$^4$ is a methyl group, R$^5$ is a hydrogen atom, and n is 3.

3. A method for producing a compound of formula (I), comprising
refluxing a compound of formula (III) and a compound of formula (IV) in a nonpolar solvent without using a base under normal or reduced pressure:

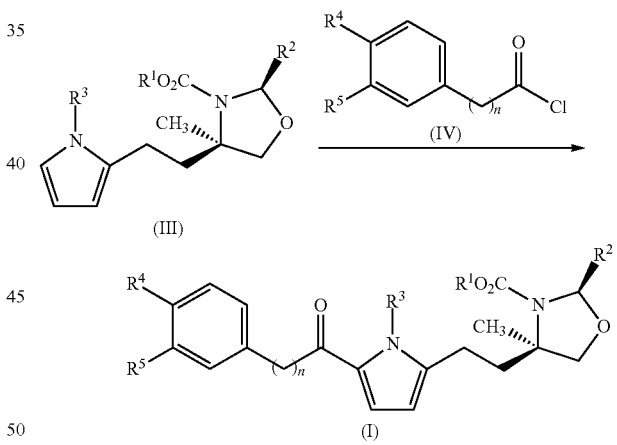

wherein
R$^1$ represents a C$_1$-C$_6$ alkyl group or a C$_7$-C$_{12}$ aralkyl group,
R$^2$ represents a group selected from the group consisting of a C$_1$-C$_6$ alkyl group, a C$_3$-C$_6$ cycloalkyl group and a C$_7$-C$_{12}$ aralkyl group,
R$^3$ represents a C$_1$-C$_6$ alkyl group,
R$^4$ and R$^5$ each independently represent a group selected from the group consisting of a hydrogen atom, a halogen atom, a C$_1$-C$_6$ alkyl group, a C$_3$-C$_6$ cycloalkyl group, a C$_1$-C$_6$ alkoxy group and a cyano group, and
n represents an integer of 1 to 6.

4. The method according to claim 3, wherein R$^1$ is a methyl group, R$^2$ is a t-butyl group, R$^3$ is a methyl group, R$^4$ is a methyl group, R$^5$ is a hydrogen atom, and n is 3.

5. A method for producing a compound of formula (II), comprising preparing a compound of formula (I) according to claim 3; and treating the compound of formula (I) with an acid and an alkali sequentially to produce a compound of formula (II):

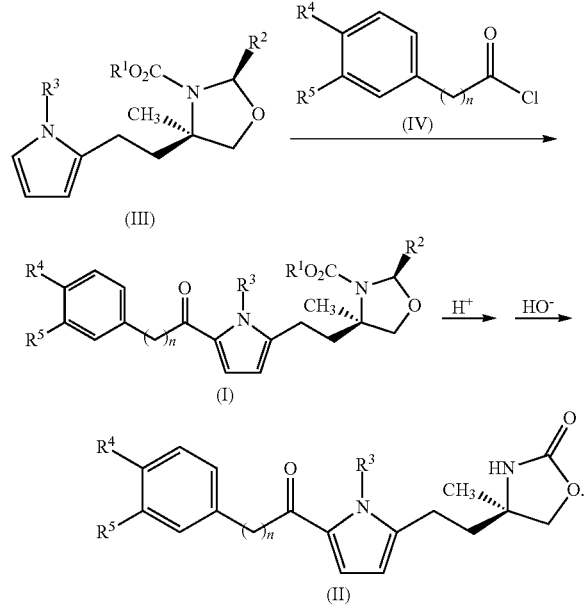

6. The method according to claim 5, wherein $R^1$ is a methyl group, $R^2$ is a t-butyl group, $R^3$ is a methyl group, $R^4$ is a methyl group, $R^5$ is a hydrogen atom, and n is 3.

7. A method for producing a compound of formula (V), comprising:

preparing the compound of formula (II) according to claim 5, and treating the compound of formula (II) with an alkali to produce a compound of formula (V):

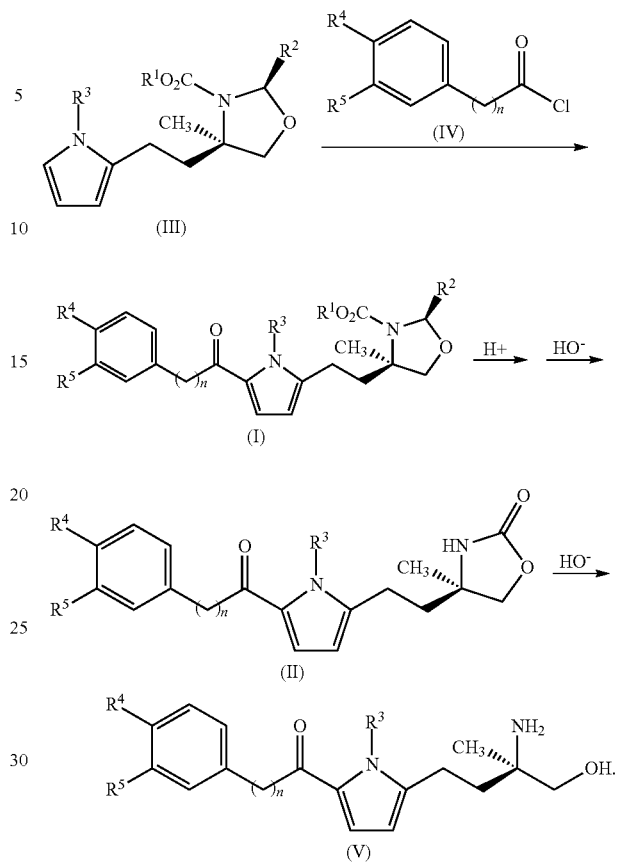

8. The method according to claim 7, wherein $R^1$ is a methyl group, $R^2$ is a t-butyl group, $R^3$ is a methyl group, $R^4$ is a methyl group, $R^5$ is a hydrogen atom, and n is 3.

* * * * *